US012788560B2

(12) United States Patent
Decker et al.

(10) Patent No.: US 12,788,560 B2
(45) Date of Patent: Nov. 10, 2026

(54) MEDICAL DEVICE DELIVERY SYSTEMS

(71) Applicant: Anteris Technologies Corporation, Eagan, MN (US)

(72) Inventors: Cedar Ray Decker, Albertville, MN (US); Christopher William Hummel, Minneapolis, MN (US); Alford Lee McLevish, Roseville, MN (US); Cameron James Albin Murto, Saint Michael, MN (US)

(73) Assignee: Anteris Technologies Corporation, Eagan, MN (US)

( * ) Notice: Subject to any disclaimer, the term of this patent is extended or adjusted under 35 U.S.C. 154(b) by 358 days.

(21) Appl. No.: 18/669,999

(22) Filed: May 21, 2024

(65) Prior Publication Data

US 2024/0390138 A1 Nov. 28, 2024

Related U.S. Application Data

(60) Provisional application No. 63/469,121, filed on May 26, 2023.

(51) Int. Cl.
*A61F 2/24* (2006.01)

(52) U.S. Cl.
CPC .................................. *A61F 2/2433* (2013.01)

(58) Field of Classification Search
CPC .......... A61F 2/24; A61F 2/2427; A61F 2/243; A61F 2/2433; A61F 2/2439
See application file for complete search history.

(56) References Cited

U.S. PATENT DOCUMENTS

| | | | | |
|---|---|---|---|---|
| 2009/0281619 A1* | 11/2009 | Le | A61M 25/01 | 623/2.11 |
| 2013/0030519 A1* | 1/2013 | Tran | A61F 2/2433 | 623/2.11 |
| 2013/0030520 A1* | 1/2013 | Lee | A61F 2/2433 | 623/2.11 |
| 2013/0123915 A1* | 5/2013 | Giannetti | A61F 2/2436 | 623/2.11 |
| 2017/0056171 A1* | 3/2017 | Cooper | A61F 2/2436 | |
| 2023/0038177 A1* | 2/2023 | Deen | A61F 2/90 | |

OTHER PUBLICATIONS

International Search Report and Written Opinion in International Appln. No. PCT/US2024/030345, mailed on Sep. 4, 2024, 18 pages.
International Preliminary Report on Patentability in International Appln. No. PCT/US2024/030345, mailed on Dec. 11, 2025, 10 pages.

* cited by examiner

*Primary Examiner* — Christopher D. Prone
(74) *Attorney, Agent, or Firm* — Fish & Richardson P.C.

(57) ABSTRACT

Delivery systems are used for medical devices. For example, this document describes delivery systems for implantable medical devices such as, but not limited to, prosthetic heart valves that are deliverable in a minimally invasive manner using a system of catheters. Some such delivery systems include a handle, a steerable catheter extending from the handle, and a balloon catheter that is slidably disposed within a lumen of the steerable catheter. The handle can include various actuators such as a first knob for actuating deflections of the steerable catheter, a balloon catheter pull rod for actuating translations of the balloon catheter, a locking mechanism for preventing translations of the balloon catheter, and/or a second knob for actuating rotations of the balloon catheter.

6 Claims, 3 Drawing Sheets

MEDICAL DEVICE DELIVERY SYSTEMS

CROSS-REFERENCE TO RELATED APPLICATIONS

This application claims the benefit of U.S. Provisional Application Ser. No. 63/469,121 filed on May 26, 2023. The disclosure of the prior application is considered part of (and is incorporated by reference in) the disclosure of this application.

BACKGROUND

1. Technical Field

This document relates to delivery systems for medical devices and methods for their use. For example, this document relates to delivery systems for implantable medical devices such as prosthetic heart valves that are deliverable in a minimally invasive manner using a system of catheters.

2. Background Information

Some prosthetic heart valves can be delivered in a minimally invasive fashion to avoid open-heart surgery. Such prosthetic heart valves can be delivered using a system of catheters that are manipulated by a clinician using an actuator handle and/or other types of control mechanisms that remain positioned external to the patient. For example, in some such cases, a prosthetic heart valve is compressed into a delivery catheter or sheath, which may be manually deflectable by adjusting a mechanism located on an actuator handle.

Transcatheter aortic valve replacement (TAVR) delivery systems can be used to deliver a prosthetic aortic valve to a native aortic heart valve site. Clinicians occasionally encounter difficulty when delivering prosthetic aortic valves in a minimally invasive manner using such catheter-based delivery systems. One such area of difficulty pertains to the task of navigating the prosthetic aortic valve through the aortic arch pathway on the way to the native aortic heart valve location.

SUMMARY

This document describes delivery systems for medical devices and methods for their use. For example, this document describes delivery systems for implantable medical devices such as, but not limited to, prosthetic heart valves that are deliverable in a minimally invasive manner using a system of catheters.

In one aspect, this disclosure is directed to a medical device system that includes a steerable catheter defining a first lumen, a pull wire comprising a distal end coupled to a distal end portion of the steerable catheter, a balloon catheter slidably disposed within the first lumen and comprising an inflatable balloon member at a distal end portion thereof, and a handle device. The handle device includes: (a) a housing; (b) a first rotatable actuator knob rotatably coupled to the housing and comprising a sleeve with an internal thread; (c) a traveler guide shaft extending internally within the sleeve, wherein a proximal end of the steerable catheter is affixed to the traveler guide; (d) a deflection nut with an external thread in engagement with the internal thread of the sleeve and defining a bore with a non-circular cross-section in which the traveler guide slidably extends, wherein a proximal end of the pull wire is coupled with the deflection nut; (c) a balloon catheter pull rod extending proximally from the housing, wherein a proximal end of the balloon catheter is affixed to the balloon catheter pull rod; (f) a locking mechanism rotatably coupled to the housing and manually adjustable between a locked position and an unlocked position, wherein the locking mechanism is configured to releasably detain the balloon catheter in relation to the housing when the locking mechanism is in the locked position; and (g) a second rotatable actuator knob rotatably coupled to the housing and configured to rotate the balloon catheter pull rod and the balloon catheter while allowing the balloon catheter pull rod to longitudinally translate in relation to the second rotatable actuator knob when the locking mechanism is in the unlocked position.

Such a medical device delivery system may optionally include one or more of the following features. The balloon catheter pull rod may be longitudinally slidable relative to the second rotatable actuator knob and the housing when the locking mechanism is in the unlocked position. The medical device delivery system may also include a collet. The balloon catheter may pass through the collet. The collet may radially compress the balloon catheter when the locking mechanism is in the locked position. The medical device delivery system may also include a deflection indicator coupled to the housing and configured to indicate visually an extent of deflection of the steerable catheter. The medical device delivery system may also include a mechanism that generates audible feedback in response to deflection of the steerable catheter.

In another aspect, this disclosure is directed to a method of delivering a prosthetic aortic valve to a patient using any of the medical device delivery systems described herein. The method includes: (1) adjusting the locking mechanism to the locked position; (2) with the locking mechanism in the locked position, advancing the medical device delivery system over a guidewire to position the prosthetic aortic valve at a location of a native aortic heart valve of the patient, wherein the advancing comprises adjusting the first rotatable actuator knob to deflect the steerable catheter and the balloon catheter in correspondence with an aortic arch of the patient; (3) with the prosthetic aortic valve at the location of the native aortic heart valve of the patient, adjusting the locking mechanism to the unlocked position; (4) with the locking mechanism in the unlocked position, pulling the housing proximally while maintaining balloon catheter pull rod in a stationary position; (5) with the locking mechanism in the unlocked position or the locked position, adjusting the second rotatable actuator knob to rotate the balloon catheter and the prosthetic aortic valve relative to the steerable catheter; (6) adjusting the locking mechanism to the locked position; (7) with the locking mechanism in the locked position, advancing or retracting the handle device, the balloon catheter and the prosthetic aortic valve to longitudinally position the prosthetic aortic valve in a desired location relative to an annulus of the native aortic heart valve of the patient; (8) inflating the balloon member to expand the prosthetic aortic valve into engagement with the native aortic heart valve of the patient; (9) deflating the balloon member; (10) adjusting the locking mechanism to the unlocked position; (11) with the locking mechanism in the unlocked position, pulling the balloon catheter pull rod proximally relative to the housing to retract the balloon catheter into the first lumen of the steerable catheter; (12) adjusting the locking mechanism to the locked position; and (13) with the locking mechanism in the locked position, retracting the handle device, the steerable catheter, and the balloon catheter from the patient.

Particular embodiments of the subject matter described in this document can be implemented to realize one or more of the following advantages. In some embodiments, the medical device delivery systems described herein are advantageously designed to enable rotary adjustments of the catheter on which the prosthetic heart valve is mounted in order to facilitate a desired alignment the of prosthetic valve's structure with the commissures of the native heart valve. In some embodiments, a steerable catheter is included as part of the medical device delivery systems described herein, and such a steerable catheter can be controllably deflected by 180° or more. Such deflection is advantageous while navigating the catheters within the patient including, navigation of the aortic arch, for example. In some such embodiments, a deflection indicator is included on the control handle of the medical device delivery systems described herein. Such an indicator is advantageous to clinicians by providing a readily available indication of the amount of deflection of the catheters that are within the patient. In some embodiments, a locking mechanism is included on the control handle of the medical device delivery systems described herein. Such a locking mechanism can be activated to advantageously lock together the catheters of the medical device delivery systems during the advancement and retraction steps of the medical device deployment process. Moreover, the locking mechanism can be unlocked to allow for relative movements of the catheters, as described herein.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

Like reference numbers represent corresponding parts throughout.

DETAILED DESCRIPTION

This document describes delivery systems for medical devices and methods for their use. For example, this document describes delivery systems for implantable medical devices such as, but not limited to, prosthetic heart valves that are deliverable in a minimally invasive manner using a system of catheters.

Figures 1, 2, 3:
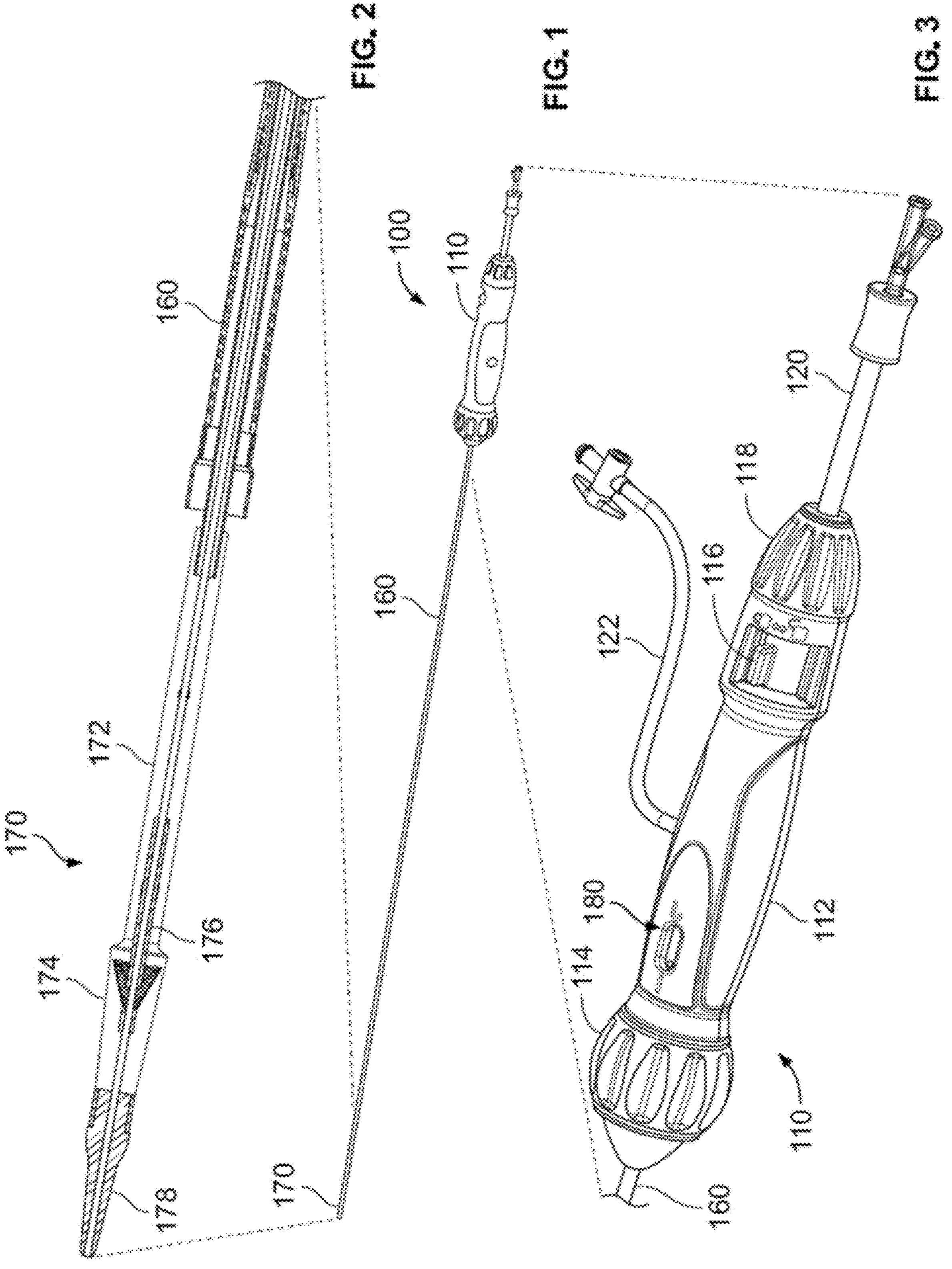
FIG. 1 is a perspective view of an example medical device delivery system in accordance with some embodiments provided herein.
FIG. 2 is an enlarged cross-section view of a distal end portion of the medical device delivery system of FIG. 1.
FIG. 3 is an enlarged view of an example handle of the medical device delivery system of FIG. 1.

FIG. 1 illustrates an example transcatheter medical device delivery system 100. In the depicted example, the medical device delivery system 100 is configured to deliver a prosthetic heart valve to a native heart valve location by advancing the prosthetic heart valve to the heart via the vascular system of the patient. For example, in some embodiments the medical device delivery system 100 can be used to deliver a prosthetic aortic valve to a site of a native aortic valve via the aorta of the patient. This non-limiting type of use of the medical device delivery system 100 is used as an example herein to describe the functionality of the medical device delivery system 100. In such a case, the medical device delivery system 100 may be inserted into a femoral artery and then advanced to the aorta, through the aortic arch, and to the native aortic valve site. Alternative approaches, such as trans-subclavian, trans-carotid, trans-radial, and others are also envisioned using the medical device delivery system 100.

Broadly speaking, the medical device delivery system 100 includes a clinician control handle 110 (or simply "handle 110"), a steerable catheter 160, and a balloon catheter 170. The steerable catheter 160 and the balloon catheter 170 each extend distally from the handle 110. The steerable catheter 160 and the balloon catheter 170 are each affixed to the handle 110, but at different locations of the handle 110 (as described further below).

FIG. 2 shows an expanded cross-sectional view of a distal end portion of the steerable catheter 160 and the balloon catheter 170. As shown, the steerable catheter 160 defines a lumen in which the balloon catheter 170 is slidably disposed. That is, the balloon catheter 170 can be manipulated by the clinician (using the handle 110) to advance and/or retract the balloon catheter 170 relative to the steerable catheter 160 by sliding the balloon catheter 170 within the lumen of the steerable catheter 160.

The steerable catheter 160 is controllably deflectable or steerable by the clinician (using the handle 110 to manipulate a pull wire 164, as described further below in reference to FIG. 4). In particular, a distal end portion of the steerable catheter 160 is controllably deflectable to any desired angle up to approximately 180°, or even more than 180° in some embodiments. When the steerable catheter 160 is deflected in that manner, the balloon catheter 170 also takes on the same extent of deflection (because the balloon catheter 170 is positioned within the lumen of the steerable catheter 160). The deflection of the steerable catheter 160 (and the balloon catheter 170) can be useful for navigating the aortic arch, for example.

Still referring to FIG. 2, the balloon catheter 170 includes a catheter shaft 172 and a balloon 174 mounted on a distal end portion of the catheter shaft 172. The wall of the catheter shaft 172 defines an inflation lumen (not visible) through which an inflation fluid can be supplied and withdrawn in order to controllably inflate and/or deflate the balloon 174. In addition, the catheter shaft 172 defines a central lumen 176 by which the balloon catheter 170 (and the steerable catheter 160) can be advanced over a guidewire. A tapered nose cone 178 extends distally from the balloon 174.

A prosthetic heart valve in a radially compressed configuration can be placed on the balloon 174. Then, when the balloon 174 and the prosthetic heart valve are positioned at a target location and in a desired orientation relative to the patient's anatomy, the balloon 174 can be inflated to radially expand the prosthetic heart valve into engagement with the native anatomy of the patient (e.g., into engagement with the annulus of a native heart valve such as the native aortic valve). Thereafter, the balloon 174 can be deflated and retracted from the prosthetic heart valve. In some embodiments, radiopaque markers can be located on one or more locations of the steerable catheter 160 and/or the balloon catheter 170 to provide visualization of the steerable catheter 160 and/or the balloon catheter 170 under fluoroscopy.

FIG. 3 shows an enlarged view of an example handle 110 of the medical device delivery system 100. The handle 110 remains external to the patient while the steerable catheter 160 and the balloon catheter 170 extend internally to the patient (e.g., into the vasculature of the patient). The handle 110 includes multiple control mechanisms by which a clinician operator can remotely manipulate various aspects of the steerable catheter 160 and the balloon catheter 170, as described further below.

In this view of the handle 110, the following components and/or control mechanisms of the handle 110 are in view. That is, the handle 110 includes a housing 112, a rotatable first actuator knob 114, a locking actuator 116, a rotatable second actuator knob 118, a balloon catheter pull rod 120, a flush line 122, and an optional deflection indicator 180. The first actuator knob 114, the second actuator knob 118, and the locking actuator 116 are each manually rotatable relative to the housing 112. The balloon catheter pull rod 120 is manually translatable relative to the housing 112 (when the locking actuator 116 is in its unlocked position, as described further below).

Figure 6:
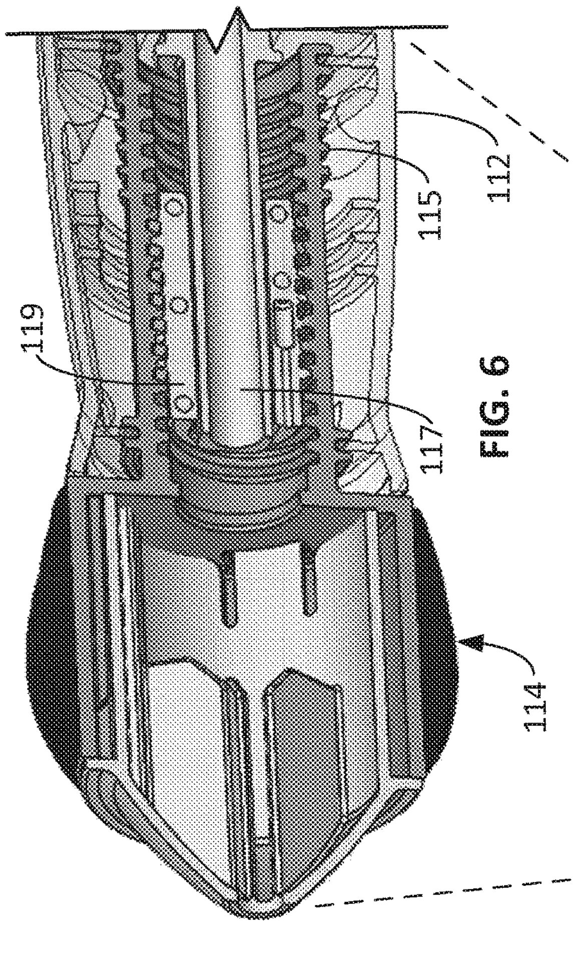
FIG. 6 is an isometric longitudinal cross-section view of an example end portion of the handle depicted in FIG. 4.
Figure 4:
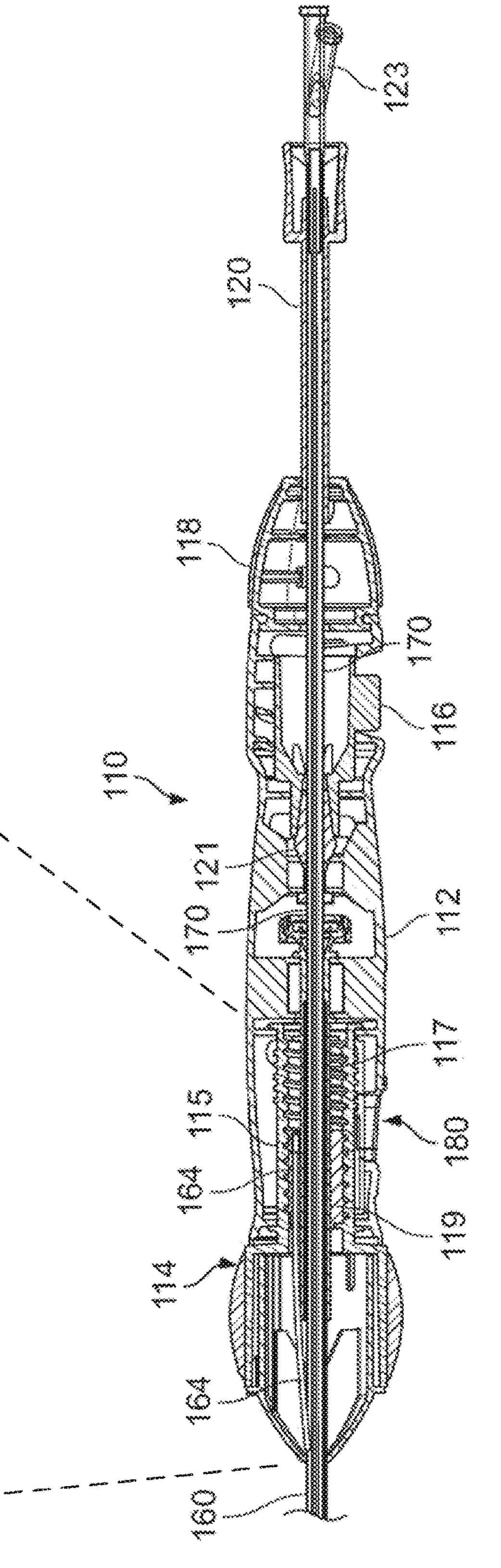
FIG. 4 is a longitudinal cross-section view of the handle of the medical device delivery system of FIG. 1.

FIGS. 4 and 6 show longitudinal cross-sectional views of the handle 110. In FIG. 6, the steerable catheter 160 and the pull wire 164 are omitted so that other internal components of the handle 110 are better visible. For example, in these views here it can be seen that the first actuator knob 114 includes (or is coupled to) a sleeve 115 with an internal thread. The sleeve 115 rotates about the longitudinal axis of the handle 110 as the first actuator knob 114 is manually rotated by a clinician.

A deflection nut 119 is movably disposed within the sleeve 115. The deflection nut 119 has an external thread in engagement with the internal thread of the sleeve 115. The deflection nut 119 defines a longitudinal bore with a non-circular cross-section (as best seen in FIG. 6).

The handle 110 also includes a traveler guide 117. The deflection nut 119 slidably translates along the traveler guide 117 as the first actuator knob 114 is manually rotated by a clinician. The non-circular shape of the external profile of the traveler guide 117 (in conjunction with the complementary non-circular shape of the bore of the deflection nut 119) allows the deflection nut 119 to slidably translate along the traveler guide 117 while resisting or preventing rotation of the deflection nut 119 relative to the traveler guide 117 and the housing 112. For example, and as depicted in FIG. 6, in some embodiments the cross-sectional shapes of the longitudinal bore of the deflection nut 119 and the external profile of the traveler guide 117 are quadrilaterals (such as a rectangle or square, etc.). Various other shapes or arrangements (e.g., other polygons, splines, key and keyway, etc.) can also be used to allow the deflection nut 119 to slidably translate along the traveler guide 117 while resisting or preventing rotation of the deflection nut 119 relative to the traveler guide 117 and the housing 112.

A proximal end of the steerable catheter 160 is affixed to the traveler guide 117. The flush line 122 is attached to the traveler guide 117 and thereby arranged to facilitate fluid flushing of the lumen of the steerable catheter 160.

The medical device delivery system 100 also includes a pull wire 164. A distal end of the pull wire 164 is coupled with a distal end portion of the steerable catheter 160. A proximal end of the pull wire 164 is coupled with the deflection nut 119. Accordingly, proximally directed translational movements of the deflection nut 119 add tension to the pull wire 164 (to cause deflection of the steerable catheter 160). Conversely, distally directed translational movements of the deflection nut 119 relax the tension of the pull wire 164 (to allow the steerable catheter 160 to elastically rebound towards its natural linear shape). Accordingly, manual rotations of the first actuator knob 114 can be used to control the extent of deflection of the steerable catheter 160 (and the balloon catheter 170 disposed therein).

As stated above, the handle 110 can optionally include a deflection indicator 180. The deflection indicator 180 has threads that are mated with external threads of the sleeve 115. Accordingly, as the first actuator knob 114 is manually rotated by a clinician, the external threads of the sleeve 115 drive the deflection indicator 180 to translate longitudinally relative to the housing 112. That translational movement of the deflection indicator 180 is visible through an opening defined by the housing 112 (sec FIG. 3). The translational movement of the deflection indicator 180 is proportional to the extent of deflection of the steerable catheter 160 (and the balloon catheter 170 disposed therein).

A proximal end of the balloon catheter 170 is affixed to the balloon catheter pull rod 120. In the depicted embodiment, the balloon catheter pull rod 120 is slidably coupled with the second actuator knob 118 using the engagement between a key and keyway arrangement. That is, in the depicted embodiment the balloon catheter pull rod 120 includes a longitudinally extending key that is slidably disposed within a longitudinally extending keyway defined by the second actuator knob 118. Accordingly, the balloon catheter pull rod 120 is longitudinally translatable relative to the second actuator knob 118 (when the locking actuator 116 is in its unlocked position) and is always constrained from rotating relative to the second actuator knob 118. Said another way, when a clinician manually rotates the second actuator knob 118 the balloon catheter pull rod 120 (and the balloon catheter 170 affixed thereto) is rotated as well. In addition, when a clinician manually pulls or pushes the balloon catheter pull rod 120 (when the locking actuator 116 is in its unlocked position), the balloon catheter 170 is moved proximally or distally relative to the steerable catheter 160 and the handle 110 as a result.

The locking mechanism of the handle 110 includes the locking actuator 116. The locking actuator 116 is rotatably coupled with the housing 112. In the depicted embodiment, the locking actuator 116 includes external threads that are engaged with threads of the housing 112. Accordingly, as a clinician rotates the locking actuator 116 relative to the housing 112, the locking actuator 116 also moves longitudinally relative to the housing 112.

The locking mechanism of the handle 110 also includes a collet 121. A portion of the balloon catheter 170 passes through the inner diameter of the collet 121. In the depicted embodiment, the portion of the balloon catheter 170 that passes through the inner diameter of the collet 121 comprises a hypo tube.

The collet 121 has a tapered outer diameter that is slidably engaged with a correspondingly tapered inner diameter of the locking actuator 116. Accordingly, as a clinician rotates the locking actuator 116 relative to the housing 112, the locking actuator 116 moves longitudinally relative to the housing 112 and the taper of the locking actuator 116 either compresses or un-compresses the collet 121 (and the portion of the balloon catheter 170 disposed within the collet 121). In that manner, manipulation of the locking actuator 116 to its locked position causes the balloon catheter 170 to be longitudinally locked in relation of the housing 112. Conversely, manipulation of the locking actuator 116 to its unlocked position causes the balloon catheter 170 to be longitudinally unlocked (and movable) in relation to the housing 112. As a point of contrast, the steerable catheter 160 is always longitudinally locked (and rotationally locked) relative to the housing 112.

When the locking actuator 116 is in its locked position, the balloon catheter 170 is longitudinally locked and therefore longitudinally immovable relative to the housing 112. However, when the locking actuator 116 is in its unlocked position, the balloon catheter 170 is longitudinally movable (by pulling or pushing the balloon catheter pull rod 120) relative to the housing 112 and the steerable catheter 160. The balloon catheter 170 is rotationally movable (by rotating the second actuator knob 118) relative to the housing 112 and the steerable catheter 160 when the locking actuator 116 is in its unlocked position and when the locking actuator 116 is in its locked position.

Figure 5:
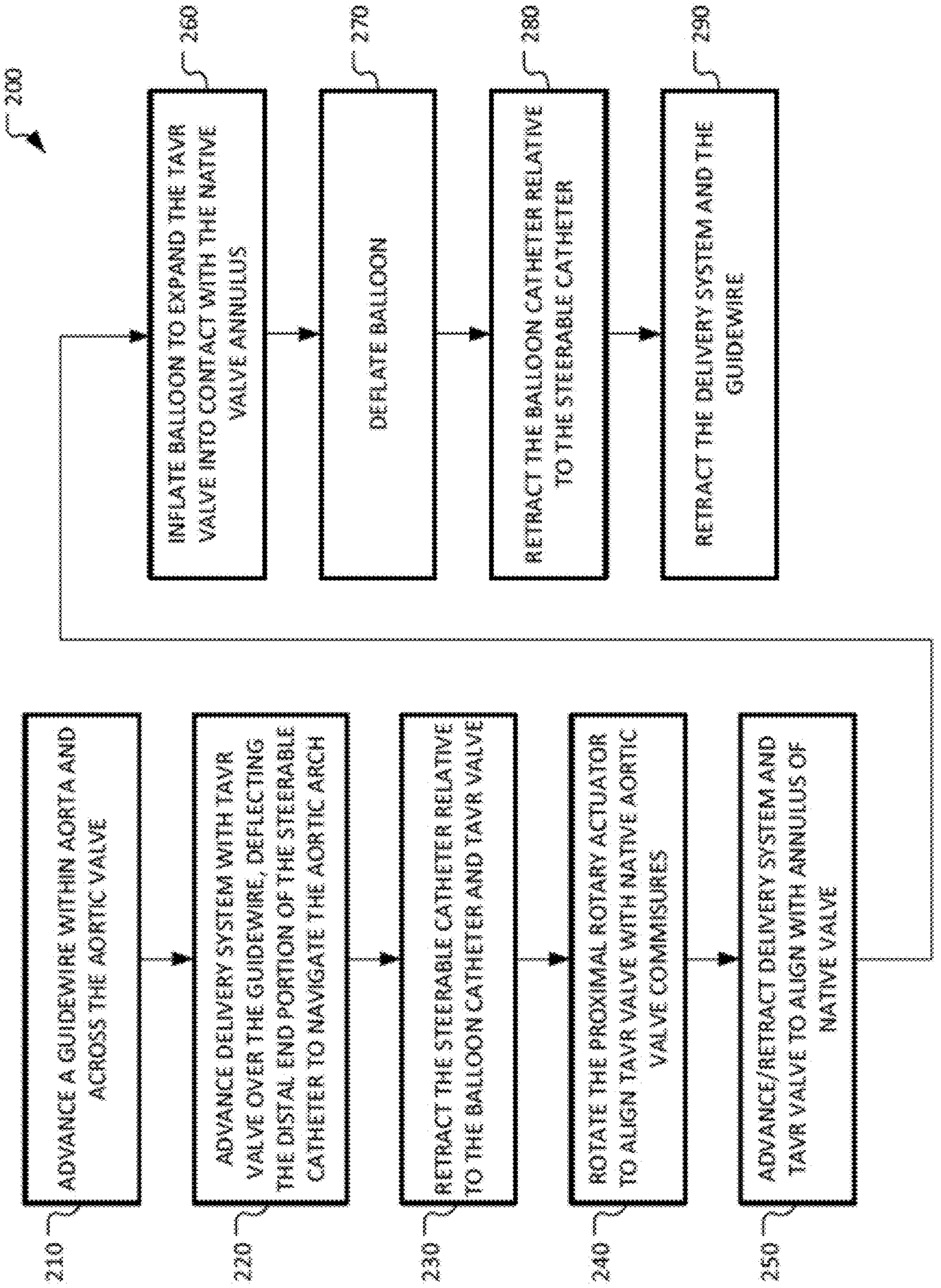
FIG. 5 is a flowchart of an example method for the delivery of a medical device in accordance with some embodiments.

FIG. 5 is a flowchart of an example method 200 for the delivery and deployment of a medical device using the medical device delivery system 100. In particular, the example method 200 is for delivering a prosthetic aortic valve using the medical device delivery system 100. Each step of the method 200 will be explained, and references will be made to FIGS. 1-4 to describe how a clinician can manipulate the medical device delivery system 100 to perform the steps of the method 200.

This method 200 can be performed by a clinician while using fluoroscopic imaging (and/or other types of imaging) in some cases. In addition, other conventional steps for preparing the medical device delivery system 100 (e.g., flushing, testing, etc.) may be performed prior to the first step 210, but are not specifically included in the flowchart of FIG. 5.

At the first step 210 of the method 200, a guidewire is inserted into the patient. For example, in some embodiments the guidewire is inserted into a femoral artery and then navigated into the aorta, over the aortic arch, and across the aortic valve. A distal end portion of the guidewire is located in the left ventricle of the patient.

At step 220, with the locking actuator 116 in the locked position, the medical device delivery system 100 (with a prosthetic aortic valve mounted in a radially compressed configuration on the balloon 174) is advanced over the guidewire. As the balloon catheter 170 and steerable catheter 160 are advanced over the aortic arch, the clinician can deflect the steerable catheter 160 (and the balloon catheter 170 contained therein) accordingly. That is, the clinician can rotate the first actuator knob 114 relative to the housing 112 to add tension to the pull wire 164, resulting in deflection of the steerable catheter 160 (and the balloon catheter 170 contained therein) to help navigate the aortic arch. The advancement of step 220 can continue until the prosthetic aortic valve is positioned generally within the native aortic valve.

At step 230, with the prosthetic aortic valve remaining positioned generally within the native aortic valve, the clinician can move the locking actuator 116 to its unlocked position and then pull the housing 112 proximally while holding the balloon catheter pull rod 120 in a generally stationary position. These actions will pull back the steerable catheter 160 relative to the balloon catheter 170 (and the prosthetic heart valve mounted thereon). The balloon catheter pull rod 120 will be extended into the housing 112 as a result.

Next, at step 240 and with the locking actuator 116 still in its unlocked position or in its locked position, the clinician can rotate the balloon catheter 170 (and the prosthetic heart valve mounted thereon) to align structural features of the prosthetic heart valve relative to anatomical features of the native aortic valve. The clinician can perform this step by rotating the second actuator knob 118 relative to the housing 112. The balloon catheter 170 will rotate in response to the rotations of second actuator knob 118, but the steerable catheter 160 will remain stationary. The clinician can use fluoroscopic imaging to observe radiopaque markers on the prosthetic heart valve to align the prosthetic heart valve in a desired orientation relative to the native heart valve anatomy (e.g., relative to commissures of the native heart valve). With the desired orientation attained, the clinician can then manipulate the locking actuator 116 to its locked position (if it was not already in the locked position).

At step 250 and with the locking actuator 116 in its locked position, the clinician can then advance or retract the medical device delivery system 100 (with the prosthetic heart valve still mounted on the balloon 174 of the balloon catheter 170) to position the prosthetic heart valve in a desired longitudinal position relative to the annulus of the native aortic valve. In some embodiments, the prosthetic heart valve can include a radiopaque marker that indicates where the prosthetic heart valve should be longitudinally located relative to the annulus of the native aortic valve. The clinician can simply push the handle 110 distally or pull the handle 110 proximally to perform this step.

At step 260 and with the locking actuator 116 still in its locked position, the clinician can then inflate the balloon 174 to expand the prosthetic heart valve into contact with the annulus of the native aortic valve. For example, the clinician can inject an inflation liquid (e.g., saline) into the inflation lumen of the balloon catheter 170 via a port 123 extending from the balloon catheter pull rod 120 to inflate the balloon 174 (and expand the prosthetic heart valve).

At step 270 and with the locking actuator 116 still in its locked position, the clinician can then deflate the balloon 174 (to uncouple the balloon 174 from the prosthetic heart valve which remains engaged with the annulus of the native aortic heart valve). To deflate the balloon 174, the clinician can withdraw the inflation liquid from the balloon 174 by performing the reverse of the injection step. Afterwards, the clinician can then manipulate the locking actuator 116 to its unlocked position.

At step 280 and with the locking actuator 116 in its unlocked position, the clinician can retract the balloon catheter 170 relative to the steerable catheter 160. To perform this, the clinician can pull the balloon catheter pull rod 120 proximally while maintaining the housing 112 generally stationary. Afterwards, the clinician can then manipulate the locking actuator 116 to its locked position.

At step 290 and with the locking actuator 116 in its locked position, the clinician can then proximally retract the medical device delivery system 100 and the guidewire from the patient to complete the method 200. The prosthetic heart valve remains engaged with the annulus of the native aortic heart valve in a functional arrangement.

Optional Features

In some embodiments, the handle 110 includes tactile and/or audible feedback that is indicative of the deflection adjustment process of the steerable catheter 160 resulting from the manipulation of the first actuator knob 114.

In some embodiments, the locking actuator 116 includes a friction member that adds friction between the locking actuator 116 and the housing 112.

In some embodiments, the deflection indicator 180 is included as part of the handle 110.

In some embodiments, a thin elastomeric coating is included on the hypo tube portion (within the housing 112) of the balloon catheter 170.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results.

What is claimed is:

1. A medical device delivery system comprising:

a steerable catheter defining a first lumen;

a pull wire comprising a distal end coupled to a distal end portion of the steerable catheter;

a balloon catheter slidably disposed within the first lumen and comprising an inflatable balloon member at a distal end portion thereof; and a handle device comprising:

a housing;

a first rotatable actuator knob rotatably coupled to the housing and comprising a sleeve with an internal thread;

a traveler guide shaft extending internally within the sleeve, wherein a proximal end of the steerable catheter is affixed to the traveler guide;

a deflection nut with an external thread in engagement with the internal thread of the sleeve and defining a bore with a non-circular cross-section in which the traveler guide slidably extends, wherein a proximal end of the pull wire is coupled with the deflection nut;

a balloon catheter pull rod extending proximally from the housing, wherein a proximal end of the balloon catheter is affixed to the balloon catheter pull rod;

a locking mechanism rotatably coupled to the housing and manually adjustable between a locked position and an unlocked position, wherein the locking mechanism is configured to releasably detain the balloon catheter in relation to the housing when the locking mechanism is in the locked position; and a second rotatable actuator knob rotatably coupled to the housing and configured to rotate the balloon catheter pull rod and the balloon catheter while allowing the balloon catheter pull rod to longitudinally translate in relation to the second rotatable actuator knob when the locking mechanism is in the unlocked position.

2. The medical device delivery system of claim 1, wherein the balloon catheter pull rod is longitudinally slidable relative to the second rotatable actuator knob and the housing when the locking mechanism is in the unlocked position.

3. The medical device delivery system of claim 1, further comprising a collet, and wherein the balloon catheter passes through the collet.

4. The medical device delivery system of claim 3, wherein the collet radially compresses the balloon catheter when the locking mechanism is in the locked position.

5. The medical device delivery system of claim 1, further comprising a deflection indicator coupled to the housing and configured to visually indicate an extent of deflection of the steerable catheter.

6. A method of delivering a prosthetic aortic valve to a patient using the medical device delivery system of claim 1, the method comprising:

adjusting the locking mechanism to the locked position;

with the locking mechanism in the locked position, advancing the medical device delivery system over a guidewire to position the prosthetic aortic valve at a location of a native aortic heart valve of the patient, wherein the advancing comprises adjusting the first rotatable actuator knob to deflect the steerable catheter and the balloon catheter in correspondence with an aortic arch of the patient;

with the prosthetic aortic valve at the location of the native aortic heart valve of the patient, adjusting the locking mechanism to the unlocked position;

with the locking mechanism in the unlocked position, pulling the housing proximally while maintaining balloon catheter pull rod in a stationary position;

with the locking mechanism in the unlocked position or the locked position, adjusting the second rotatable actuator knob to rotate the balloon catheter and the prosthetic aortic valve relative to the steerable catheter;

adjusting the locking mechanism to the locked position;

with the locking mechanism in the locked position, advancing or retracting the handle device, the balloon catheter and the prosthetic aortic valve to longitudinally position the prosthetic aortic valve in a desired location relative to an annulus of the native aortic heart valve of the patient;

inflating the balloon member to expand the prosthetic aortic valve into engagement with the native aortic heart valve of the patient;

deflating the balloon member;

adjusting the locking mechanism to the unlocked position;

with the locking mechanism in the unlocked position, pulling the balloon catheter pull rod proximally relative to the housing to retract the balloon catheter into the first lumen of the steerable catheter;

adjusting the locking mechanism to the locked position; and with the locking mechanism in the locked position, retracting the handle device, the steerable catheter, and the balloon catheter from the patient.

* * * * *